United States Patent [19]
Agarwal et al.

[11] Patent Number: 6,086,889
[45] Date of Patent: Jul. 11, 2000

[54] **PROCESS FOR THE ISOLATION OF Z AND E GUGULSTERONES FROM AERIAL BRANCHES OF *COMMIPHORA WIGHTII* (GUGGUL)**

[75] Inventors: Santosh Kumar Agarwal; Tajuddin; Mohammad Shafiq Siddiqui; Sushil Kumar; Ashok Kumar Khanna; Ramesh Chander, all of Lucknow, India

[73] Assignee: Council of Scientific & Industrial Research, New Delhi, India

[21] Appl. No.: 09/263,204

[22] Filed: Mar. 5, 1999

[30] Foreign Application Priority Data

Feb. 12, 1999 [IN] India ................................. 242 Del/99

[51] Int. Cl.[7] .............................. A61K 31/57; C07J 13/00
[52] U.S. Cl. ...................................... 424/195.1; 424/196.1
[58] Field of Search .............................. 424/195.1, 196.1

[56] References Cited

PUBLICATIONS

Bhatt et al., "Enhancement of Oleo–Gum Resin Production in *Commiphora wightii* by Improved Tapping Technique", Current Science, Apr. 5, 1989, vol. 58, No. 7, pp. 349–357.

Satyavati, *Medicinal Plants of India*, vol. I, pp. 270–276, 1976.

Patil et al., "Chemistry of Ayurvedic Crude Drugs", Tetrahedron 28, 2341, 1972.

Chemical Abstracts 85:256t, 1976.

Chemical Abstracts 116:67242n, 1992.

*Primary Examiner*—Gary L. Kunz
*Attorney, Agent, or Firm*—Wenderoth, Lind & Ponack LLP

[57] ABSTRACT

A process for the isolation of a lipid fraction containing Z & E guggulsterones useful as cholesterol lowering drug, which comprises soaking/soxhlet extracting the powdered aerial part of the plant *C. wightii* with a non polar solvent, filtering/deanting the extract, soaking the material again in a polar solvent, filtering and concentrating the extracted material under reduced pressure as to obtain a thick viscous extract, and subjecting the thick viscous extract to gel filteration/silica gel chromatography to obtain Z & E ketosteroid containing lipid fraction exhibiting hypolipidemic activity.

8 Claims, No Drawings

6,086,889

PROCESS FOR THE ISOLATION OF Z AND E GUGULSTERONES FROM AERIAL BRANCHES OF *COMMIPHORA WIGHTII* (GUGGUL)

FIELD OF INVENTION

The present invention relates to a process for the isolation of a lipid fraction containing Z & E guggulsterones useful as cholesterol lowering drug from aerial branches of *Commiphora wightii* (guggul). More particularly, this invention relates to obtaining a lipid fraction from branches (stems) of *C. wightii* having hypolipidemic activity instead of getting the same from its gum resin.

BACKGROUND OF INVENTION

Guggul (*C. wightii*) is distributed mainly in Gujarat and Rajasthan states of India. It is cultivated for the oleo-gum resin which has wide application in allopathic, ayurvedic and unani system of medicine. E and Z guggulsterones used as markers for standardization of lipid fraction associated with other complex lipids of this resin (having similar polarities) are of interest from this oleo-gum-resin as they produce drug for etheroscelrosis. The drug has also achieved prominence due to its anti-inflammatory, anti-rheumatic, anti-arthritis, hypo-cholesteremic, hypolipidimic and anti-fertility activities. Its extract also reduces serum cholesterol and effects catecholamine metabolism considerably. A cholesterol lowering drug, prepared from guggul-gum-resin of *C. wightii* is in the market under the trade name Guglip. Guggul is collected from the wild untended plants by tribal people by the traditional tapping methods used to obtain guggul of *C. wightii*. However, few improved tapping techniques used 'mitchie golledge', knife coupled with ethephon (2-chloroethyl phosphoric acid and ethelene releasing synthetic chemical) application has been devised. This method could enhance guggul production but again the tapping injures the plant resulting in drying up the plant recognizing the rapid and extensive depletion of the natural population of *C. wightii*, this species has been listed as a threatened plant of India (Current Science 58, 349–357, 1989, references cited therein). India used to produce over 40 tons of guggul gum from the arid tracts of Rajasthan and Gujarat states. Now a mere 4–5 tons of the gum is being traded there. Other methods so far developed by researchers, though relate to get some more guggul gum, however, not much attention is paid to save the plant. Further, no improvement programme for guggul gum plant has been taken up to identify a superior clone having higher guggulsterones from the genetic resources of guggul plant available in Rajasthan and Gujarat, India.

Thus, we have made efforts to develop a non destructive method of obtaining the desired hypolipidemic drug from the aerial part of *C. wightii*. The plant can be pruned each year without damaging it which will ensure the constant supply of the crude drug. Starting from 5th year of plant, about 10 kg of dry branches can be obtained each year from each plant.

Number of reviews and research papers have appeared in various journals where the detailed chemistry of guggul gum resin and it's pharmacological properties have been discussed. However, there is no report where they have obtained hypolipidemic lipid fraction from *C. wightii* stems (G. V. Satyavati, Medicinal Plants of India, Vol. , 270–276, 1976).

Guggulu, the gum resin exudate from *C. wightii* is a complex mixture of steroids, diterpenoids, aliphatic esters, carbohydrates and a variety of inorganic ions besides minor amount of sesamin and other unidentified constituents (Tetrahedron 28, 2341 1972).

In one of the methods guggulsterones were isolated from the neutral fraction after saponification of the chloroform extract of guggul gum (*C. wightii*) and their structures were determined (J. Res. Indian Med. 10(2), 11, 1975).

In one of the method guggul gum resin was extracted with ethyl acetate and this fraction was divided equentially in neutral, acidic and basic fractions and then the neutral fraction was again divided into ketonic and non-ketonic fraction The non-ketonic fraction was subdivided into by partitioning between hexane-90% aqueous methanol. This methanol fraction was diluted by adding water to 50% methanol and partitioned with benzene to get benzene phase and 50% aq. MeOH phase. Out of these fractions, the hypolipidemic activity was located in neutral, acidic and basic fractions. (G. V. Satyavati, Medicinal Plants of India, Vol. I, 270–276, 1976, reference cited therein).

In another report, hypolipidemic properties of keto-steroids from guggul gum resin has been discussed (C.A. 85: 256, (1976)).

A patent on hypolipidemic tablets containing guggul lipid from guggul gum resin is in literature (C.A. 116: P 67242, 1992).

Indina Patent No. 148265 describes a process wherein guggul gum resin was repeatedly extracted with ethyl acetate and the extract after concentration was divided into acidic, basic and neutral fractions. The neutral fraction contained Z and E guggulsterones and other lipids which were responsible for cholesterol lowering activity. Other compounds such as guggul sterols exhibiting synergistic hypolipidemic effect were also present. Routine standardization of guggul lipid prepared from resin samples was done on the basis of concentration of Z & E guggul sterones as markers present in it by using HPLC.

Pure guggul gum resin usually contains 1 to 1.5% of Z and E guggulsterones and from a 10 to 15 years old guggul plant, 300 to 400 gm of the gum is obtained on deep incision in the plant trunk. Central Drug Research Institute, (CDR) Lucknow, India has marketed the process as described earlier to a pharmaceutical company under the trade name GUGULIP for commercial exploitation.

OBJECT OF THE INVENTION

The main object of the present invention is to provide a process for the isolation of a lipid fraction containing Z & E guggulsterones useful as cholesterol lowering drug from aerial branches of *Commiphora wightii* (guggul) which obviates the draw backs as detailed above.

SUMMARY OF INVENTION

The present invention shows the presence of Z & E guggulsterones along with other lipids in the aerial part (stems) of *C. wightii* plant and a methodology has been worked out for obtaining a lipid lowering fraction from the aerial part of this plant. The lipid fraction thus obtained contains Z & E gugglsterones and other sterols etc. Further initial biological screening of this lipid fraction has shown promising hypolipidemic activity. It is our first report and is a new invention.

DETAILED DESCRIPTION OF THE INVENTION

Accordingly, the present process for the isolation of a lipid fraction containing Z & E guggulsterones useful as cholesterol lowering drug from aerial branches of *Commiphora wightii* (guggul) which comprises, soaking/soxhlet extracting the powdered aerial part of the plant *C. wightii* with any of the non-polar solvent and filtering/decanting it, followed by soaking the material again in polar solvent, filtering and concentrating the extracted material under reduced pressure as to obtain a thick viscous extract, which is subjected to gel filteration/silica gel chromatography to obtain Z & E ketosteroids containing lipid fraction exhibiting hypolipidemic activity.

The invention relates to a process for obtaining lipid fraction containing Z & E guggulsterones useful as cholesterol lowering drug from aerial branches of *C. wightii* has been disclosed. Hypolipidemic activity of the fraction has been established in triton model in rats indicating the percent lowering in serum lipids. The process has the advantage due to the use of the aerial part of the plant thereby the drug can be obtained over a period of several years. Otherwise in the process of obtaining the lipid fraction from guggul gum resin which is obtained from 10–15 years old plant by tapping the main trunk thereby leading to the death of plants. The method is simple and commercially feasible.

One embodiment of the invention relates to a process for the isolation of a lipid fraction containing Z & E guggulsterones useful as cholesterol lowering drug, which comprises, (i) soaking/soxhlet extracting the powdered aerial part of the plant *C. wightii* with a non polar solvent,
(ii) filtering/deanting the extract,
(iii) soaking the material again in a polar solvent,
(iv) filtering and concentrating the extracted material under reduced pressure as to obtain a thick viscous extract; and
(v) subjecting the thick viscous extract to gel filteration/silica gel chromatography to obtain Z & E ketosteroid containing lipid fraction exhibiting hypolipidemic activity.

In another embodiment of the process, the non polar organic solvents is selected from petroleum ether and their fractions like hexane, benzene, chlorinated solvents etc. and polar solvents such as ethanol, methanol, propanol, butanol, etc., and their isomers may be used.

In another embodiment of the process organic eluants used for the purification of the gummy extract through silica gel/gel filteration column are selected from ethyl acetate, alcohols (e.g. methanol, ethanol, propanol).

TABLE 1

Hypolipidemic activity of guggul lipid in Triton model in rats.
Dose (100 mg/kg, p.o.)

| | Percent lowering serum lipids | | |
|---|---|---|---|
| | Total cholesterol | Phospholipids | Triglycerides |
| Guggul lipid (stem) Example-1 | 38 | 22 | 29 |
| Guggul lipid (stem) Example-2 | 33 | 21 | 24 |
| Guggul lipid (CDRI Standard drug) | 34 | 25 | 36 |

Lipid fractions exhibited hypolipidemic activity (Table-1) almost of the same order as that of the guggul lipid (control).

The following examples serve to describe the process of the present invention in detail. This example is not to be construed as limiting the invention as these are given by way of illustrating the invention.

EXAMPLE 1

*C. wightii* stems (100 g) were shade dried, powdered and extracted with methanol in a continuous extractor for 24 hrs. The extract was filtered to remove suspended impurities if any and concentrated to dryness (wt. 2.8 g). The green gummy extract was macerated with benzene three times (100 ml each) and acetone-ether (1:1) mixture (100 ml×3 times) successively. The later fraction contained mainly ketosteroids and other lipids along with resinous impurities. This fraction was concentrated to a thick brown mass, taken into ethyl acetate (10 ml) and passed through a bed of silica gel (25 ml) using ethyl acetate-methanol (3:1) as eluant. This eluate was concentrated to brown mass containing mainly guggulsterones and other lipids. The overall yield was 0.5% based on dry wt. of aerial part. The former benzene fraction was rejected.

EXAMPLE 2

Dried powdered *C. wightii* stems (100 g) as in example 1 was soaked in ethanol:H2O (95:5) at room temperature for a week and the extract was decanted. This soaking was repeated three times with pure ethanol:H2O (95:5) and the soaking time was reduced to 24 hours. All the four extracts were combined and solvent was removed under reduced pressure to get a thick green brown paste (weight 2.9 g).

This paste was dissolved in methanol and suspended impurities were filtered off. This was concentrated to 5 ml and passed through a bed of LH-20 gel (50 g) and 20 fractions of 15 ml each were collected. Fractions 6 to 15 contained ketosteroids and other lipids responsible for hypolipidemic activity. Other fractions from 1 to 5 and 16–20 were rejected as impurities. These were combined and concentrated to a light brown sticky mass the overall yield based on dry weight of the aerial part was 0.6%.

EXAMPLE 3

*C. wightii* were choaked and shaked dry and 200 g of this plant material was filled in a soxhlet. The material was continuously extracted with hexane (500 ml) for 12 hours followed by extraction with ethyl acetate-chloroform (1:1) mixture (500 ml) for 12 hours. The hexane extract after extracting to recover hexane was rejected and the later extract was concentrated under reduced pressure to get green gumming extract (5.2 gm). It was taken in a minimum amount of ethyl acetate (100 ml) and chromatographed over silica gel (60–120 mesh, 35 g) column packed in ethyl acetate. In all ten fractions (25 ml) each were collected. Fractions (4–7) which contained Z & E guggulsterones and other lipids were mixed together and solvent was evaporated under reduced pressure. The overall yield of lipids was 0.46% based on dry weight of branches.

EXAMPLE 4

*C. wightii* branches (100 g) were air dried, powdered and soaked into petroleum ether (4–0–60° C., 500 ml) at room temperature (25° C.) for two days. The petroleum ether extract was filtered through a cotton plug. It was repeated three times. The petroleum ether extracts were rejected. The extracted plant material was extracted with a mixture of ethyl acetate MeOH (9:1,500 ml×3 times) at room temperature. The total ethyl acetate MeOH extract was concentrated under reduced pressure to get a brown green viscous mass (4.1 gm). This extract was dissolved in 10 ml of ethyl acetate and chromatographed over silica gel column (60–120 mesh, 40 gm) using ethyl acetate, ethyl acetate : methonol (9:1) as eluent. In all 15 fractions (25 ml each) were eluted. Fractions (5–8) showing spots of Z & E guggulsterones of TLC (SiO2) plates along with lipid streak were combined and concentrated under reduced pressure to get lipid fraction containing Z & E guggulsteronoes in an yield of 0.2% based on dry weight of stems.

ADVANTAGES OF THE PRESENT INVENTION

Lipid fraction containing Z & E guggulsterones is obtained from the stem part of the plant thereby saving the plants which otherwise die due to deep incisions given to collect the guggulgum. The 10–15 years old *C. wightii* plant is used for obtaining the gum resin which normally dies due to deep incision in the main trunk and thereby it is of one time method.

Lipid fraction containing Z & E guggulsterones can be obtained over a period of several years, by taking the aerial part (about ¾th of the herbage) of the said plant each year thereby having a sustained supply of raw materials over the years.

The method does not require sophisticated equipments and steps are simple, economical and commercially feasible.

We claim:

1. A process for the isolation of a lipid fraction containing Z and E guggulsterones useful as cholesterol lowering drug, which comprises,
    (i) soaking or soxhlet extracting the powdered aerial part of the plant *C. wightii* with a nonpolar solvent,
    (ii) filtering or decanting the extract,
    (iii) soaking the material again in a polar solvent,
    (iv) filtering and concentrating the extracted material in the polar solvent under reduced pressure as to obtain a thick viscous extract, and
    (v) subjecting the thick viscous extract to gel filtration or silica gel chromatography to obtain Z and E ketosteroid containing lipid fraction exhibiting hypolipidemic activity.

2. The process of claim 1, wherein said nonpolar organic solvent is selected from the group consisting of petroleum ether, petroleum ether fractions, hexane, benzene, and chlorinated solvents.

3. The process of claim 1, wherein said polar solvent is selected from the group consisting of ethanol, methanol, propanol, butanol, and their isomers.

4. The process of claim 1, wherein said nonpolar solvent is petroleum fractions.

5. The process of claim 1, wherein said polar solvent is ethyl acetate.

6. The process of claim 1, wherein the filtering and concentrating of the extract is carried out under a pressure of between 20–50 mm of Hg.

7. The process of claim 1, wherein an organic eluant is used in the purification of the thick viscous extract through either silica gel or gel filtration column chromatography and the organic eluant is selected from the group consisting of ethyl acetate, methanol, ethanol, and propanol.

8. The process of claim 1, wherein the lipid fraction containing Z and E guggulsterones is extracted from the aerial branches of *Commiphora wightii* (guggul).

* * * * *